United States Patent
Roche

(10) Patent No.: US 8,498,711 B2
(45) Date of Patent: *Jul. 30, 2013

(54) POST-OPERATIVE PAIN INHIBITOR FOR JOINT REPLACEMENT AND METHOD THEREOF

(76) Inventor: Martin William Roche, Fort Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/310,436

(22) Filed: Dec. 2, 2011

(65) Prior Publication Data

US 2012/0078324 A1   Mar. 29, 2012

Related U.S. Application Data

(63) Continuation of application No. 12/604,099, filed on Oct. 22, 2009, now Pat. No. 8,099,168.

(60) Provisional application No. 61/196,916, filed on Oct. 22, 2008, provisional application No. 61/196,915, filed on Oct. 22, 2008, provisional application No. 61/196,914, filed on Oct. 22, 2008.

(51) Int. Cl.
*A61N 1/00* (2006.01)

(52) U.S. Cl.
USPC ............................................................. 607/46

(58) Field of Classification Search
USPC .................. 607/46, 41, 11, 2, 67, 51
See application file for complete search history.

(56) References Cited

U.S. PATENT DOCUMENTS

| | | | |
|---|---|---|---|
| 5,702,429 A | 12/1997 | King | |
| 6,014,588 A | 1/2000 | Fitz | |
| 6,493,588 B1 | 12/2002 | Malaney et al. | |
| 6,505,075 B1 | 1/2003 | Weiner | |
| 7,580,753 B2 | 8/2009 | Kim et al. | |
| 7,917,223 B2 * | 3/2011 | Madjar et al. | 607/51 |
| 2005/0176823 A1 | 8/2005 | Diaz | |
| 2006/0030906 A1 * | 2/2006 | Carroll | 607/67 |
| 2006/0052844 A1 * | 3/2006 | Newman | 607/67 |
| 2006/0093646 A1 | 5/2006 | Cima et al. | |
| 2006/0167512 A1 * | 7/2006 | Ross et al. | 607/11 |
| 2007/0060975 A1 * | 3/2007 | Mannheimer et al. | 607/46 |
| 2007/0213771 A1 * | 9/2007 | Spinner et al. | 607/2 |
| 2009/0326602 A1 * | 12/2009 | Glukhovsky et al. | 607/41 |
| 2010/0198298 A1 | 8/2010 | Glukhovski et al. | |
| 2010/0204749 A1 | 8/2010 | Thimineur et al. | |

* cited by examiner

Primary Examiner — George Manuel
Assistant Examiner — Robert N Wieland

(57) ABSTRACT

A post-operative pain inhibitor system comprises a controller and leads. Neuro-stimulator circuitry may be included within the patient controller or within one or more prosthetic components for generating a signal. In one example, an electrode is configured to be attached to skin in proximity to an operative field of an implanted joint. Topical leads, percutaneous leads, subcutaneous leads, intraosseous leads, or leads can also be placed in proximity to the operative field corresponding to the prosthetic component installation. The lead or electrodes can be coupled to neuro-stimulation circuitry to stimulate peripheral nerve fibers to affect body generated action potentials. A transmitter or power source can be housed in a prosthetic component. The controller can modify the pulse width, pulse shape, pulse repetition rate, and pulse amplitude of the signal thereby allowing the patient to adapt the signal to minimize their perceived pain.

18 Claims, 7 Drawing Sheets

POST-OPERATIVE PAIN INHIBITOR FOR JOINT REPLACEMENT AND METHOD THEREOF

CROSS-REFERENCE TO RELATED APPLICATIONS

This application is a Continuation of U.S. application Ser. No. 12/604,099 filed on Oct. 22, 2009 claiming priority benefit of the U.S. Provisional Patent Application No. 61/196,916, U.S. Provisional Patent Application No. 61/196,915, and U.S. Provisional Patent Application No. 61/196,914 all filed on Oct. 22, 2008, the entire contents of which are hereby incorporated by reference.

FIELD

The invention relates in general to pain treatment in living organisms, and particularly though not exclusively, is related to post-operative pain reduction after joint replacement.

BACKGROUND

Implantable devices are becoming more prevalent. Complex mechanical and electrical systems such as pacemakers, heart defibrillators, orthopedic implants, neurological devices are but a few of the systems being implanted on a common basis. Implantable devices have proven reliable and are placed inside the human body for extended periods. Orthopedic implants are typically used to repair a damaged joint or bone in a skeletal system. Orthopedic surgery comprises at least one incision to access the joint region. In a complete joint replacement, bone is cut in the joint region and the articulating surfaces of the joint are replaced.

Pain is a substantial issue associated with joint implantation. In fact, knee replacement is known to be one of the most painful surgeries to the patient. Pain is controlled both pre-operatively, intra-operatively, and post-operatively. Narcotic medication is still a widely used choice to control pain in a complete joint replacement. Narcotic pain control varies from patient to patient. The patient response to the medication can have side effects such as nausea, vomiting, itching, ileus, confusion, respiratory problems, and depression to name a few. In general, these side effects can affect patient recovery both short term and long term.

BRIEF DESCRIPTION OF THE DRAWINGS

Exemplary embodiments of present invention will become more fully understood from the detailed description and the accompanying drawings, wherein:

FIG. 10 illustrates a hip prosthesis in accordance with an exemplary embodiment and FIG. 11 illustrates a tibial implant in accordance with an exemplary embodiment;

FIG. 10 is an illustration of a hip prosthesis in accordance with an exemplary embodiment;

FIG. 11 is an illustration of a tibial implant 14 in accordance with an exemplary embodiment;

DETAILED DESCRIPTION

Figure 1:
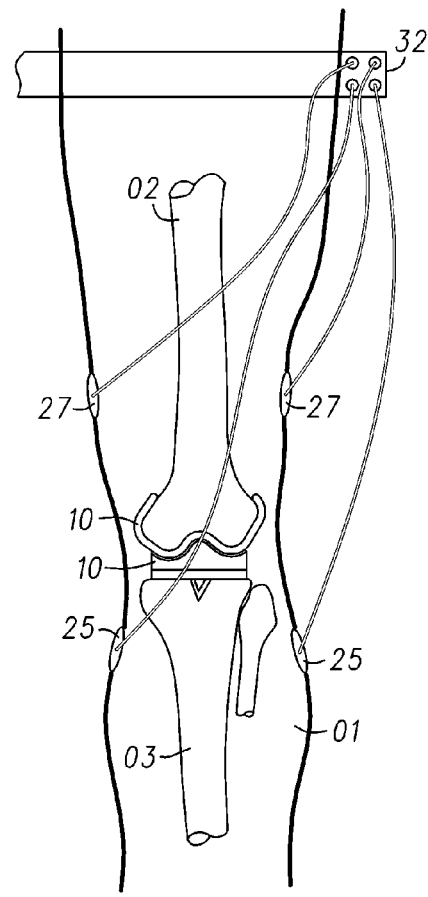
FIG. 1 is an illustration of a pain modulation system for post-operative pain treatment of a skeletal system in accordance with an exemplary embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally, the sizes of structures used in exemplary embodiments are not limited by any discussion herein (e.g., the sizes of structures can be macro (centimeter, meter, and greater in size), micro (micro meter), nanometer size and smaller).

Notice that similar reference numerals and letters refer to similar items in the following figures, and thus once an item is defined in one figure, it may not be discussed or further defined in the following figures.

In all of the examples illustrated and discussed herein, any specific values, should be interpreted to be illustrative only and non-limiting. Thus, other examples of the exemplary embodiments could have different values.

In general, the successful implantation of a device in an organism and more specifically in a joint or spine depends on multiple factors. One factor is that the surgeon strives to implant the device to obtain adequate alignment of the extremity or spine. A second factor is proper seating of the implant for stability. A third factor is that orthopedic implants typically comprise more than one component that are aligned in relation to one another. A fourth factor is balance of loading over a range motion. A fifth factor and a more general factor that relates to all implanted devices is to minimize infections that can occur post-operatively. A sixth factor is post-operative pain. Implant surgery can result in substantial pain to the patient. Pain can affect the quality of life of the patient and increase the time for rehabilitation.

A post-operative pain Inhibitor (PPI) is described herein below that integrates peripheral nerve inhibition in the local post-operative field of the implanted joint. The PPI is a pain modulation system that can be used in conjunction with the skeletal system and more specifically with an artificial joint implantation. For illustrative purposes, a knee implant and a hip implant are used to show the operation of the pain inhibitor system. A knee implant is known for being one of the more painful implant surgeries. In general, the PPI is used to alleviate pain related to the skeletal system and can be used for joint implants such as, but not limited to, knee, hip, shoulder, spine, ankle, wrist, prosthetic devices, articulating, and non-articulating bone structures.

FIG. 1 is an illustration of a post-operative pain inhibitor system 100 for post-operative pain treatment of a skeletal system. In a non-limiting example, a lateral view of a leg is illustrated after a knee replacement surgery has been performed. At least one incision in skin 1 is used to expose the joint region. The incision gives access to a femur 2 and a tibia 1. A knee prosthesis or joint implant 10 typically comprises a femoral implant, an insert, and a tibial implant. A distal end of a femur 2 is prepared and receives the femoral implant. In a full knee replacement, the femoral implant has two condyle surfaces that mimic a natural femur. The femoral implant is typically made of a metal or metal alloy. Similarly, a proximal end of tibia 3 is prepared to receive the tibial implant. The tibial implant is a support structure that is fastened to the proximal end of tibia 3 and is usually made of a metal or metal alloy. An insert is fitted between the femoral implant and tibial implant. In the full knee replacement, the insert has two bearing surfaces in contact with the two condyle surfaces of the femoral implant that allow rotation of the lower leg under load. The tibial implant retains the insert in place. The insert is typically made of a high wear polymer that minimizes friction.

Post-operative pain inhibitor system 100 comprises a controller 32 coupled to topical leads 27 and percutaneous leads 25. System 100 can address pain control during and after joint replacement. Pain affects a patient's recovery and hinders early joint function. Common effects of pain following total knee replacements include depression, tachycardia, insomnia, reflex muscle spasm and sometimes chronic regional pain syndromes. Research has shown that pre-operative pain control has a positive effect on the severity of pain post-operatively. Intra-operative anesthetic control is critical. Narcotic medication is still needed for joint implants and especially for total knee replacements. Pain control is variable and the common side effects (nausea, vomiting, itching, ileus, confusion, respiratory depression) often interfere with rapid recovery. Post-operative pain inhibitor system 100 can reduce reliance on other pain control methods or be used in conjunction with the methods to deliver a more consistent and higher level of pain reduction.

In at least one exemplary embodiment, one or more leads are placed in proximity to the operative field of the implanted joint. Controller 32 is shown connected by wire to topical lead 25 and percutaneous leads 27. Controller 32 provides a signal to leads 25 and 27. Leads 25 and 27 are used to transfer pulses of electrical energy to stimulate peripheral nerve fibers to inhibit or block a pain signal thereby reducing the perceived pain by the patient. Either type of lead may be used, or both types may be used in combination, to achieve adequate pain control.

In general, a low amplitude current is used to stimulate the peripheral nerve fibers. Topical lead 27 and percutaneous leads 25 are current injecting components that receive a signal from controller 32. Topical leads 27 are placed on a surface of skin 1 to make electrical contact. Percutaneous leads 25 include a contact region that punctures or couples through the outer skin layer to make contact. Leads 25 and 27 are attached to a predetermined position on the patient's body which is typically in the vicinity, but not limited to the operative field where the orthopedic device was implanted and a peripheral nerve fiber.

The lateral view of the leg illustrates two embodiments of a wired electrical connection from neuro-stimulator circuitry of controller 32 to stimulate peripheral nerves for the inhibition of pain. A first embodiment comprises a placement of topical leads 27 with a wired connection to controller 32. The second embodiment is the placement of a percutaneous lead 25 with a wired connection to controller 32. In both cases the electrical pulses travel through external wires to terminate in the lead affixed to the patient's skin 1. In the case of the knee implant, leads 25 and 27 are shown contacting skin 1 in proximity to the implanted knee. Leads 25 and 27 provide an electrically conductive contact to the skin in which to direct the current to the peripheral nerve fiber. The low amplitude pulsed current provided by the neuro-stimulator circuitry of controller 32 blocks the propagation of body generated action potentials.

Pain signals are carried by small, slow conducting peripheral nerve fibers (C-fibers). The pain signals can be blocked by stimulation of the large diameter, rapidly conducting peripheral nerve fibers (A-fibers). The balance between A and C-fibers determines the degree of pain. Stimulation of A-fibers by a variety of stimuli (scratching, pressure, vibration, or electrical stimulation) with little or no stimulation of C-fibers will close the gate. Thus, controller 32 in conjunction with leads 25 and 27 stimulate the A-fibers with a current pulse to close the gate and block the propagation of pain signals carried by the C-fibers thereby reducing perceived pain by the patient.

In at least one exemplary embodiment, a bipolar electrode device can be used to electrical contact skin 1 and deliver a signal to inhibit a body generated pain signal propagating in a peripheral nerve fiber. The bipolar electrode device corresponds to leads 25 and 27. The bipolar electrode device has an anode and a cathode. In a non-limiting example, the anode of the bipolar electrode device is placed in close proximity to the peripheral nerve fiber and the operative field. The cathode of the bipolar electrode device is placed away from the anode in a region of low sensitivity. Sufficient energy is provide by controller 32 to hyperpolarize the peripheral nerve fiber.

Alternatively, a tri-polar electrode device can be used to selectively block the propagation of body generated action potentials traveling through a nerve bundle. The tri-polar electrode device corresponds to leads 25 and 27. The tri-polar electrode device comprises a first anode, a second anode, and a cathode. In a non-limiting example, the cathode is placed between the first and second anodes. A pulse is provided to the peripheral nerve fiber from both anodes. The cathode can be placed non-equidistant between the anodes. The signals provided by each anode can be different. The tri-polar electrode generates a uni-directional action potential to serve as collision block with body-generated action potentials representing pain sensations in the small-diameter sensory fibers of a peripheral nerve fiber.

In at least one exemplary embodiment, controller 32 is accessible to the patient. It should be understood that each patient is different and each will have varying ability to cope with pain. Furthermore, placement of the leads 25 and 27 and the conducting distance will also vary. In a non-limiting example, controller 32 couples to a belt that can be wrapped and held at the waist of the patient. Controller 32 includes controls such as dials, switches, a keyboard, a touch panel, touch screen, or a wireless interface. The controls on controller 32 are used to modify the signal provided to leads 25 and 27. The controls of controller 32 are coupled to a logic unit, a signal generator, a power source, and communication circuitry to generate electrical impulses tailored to an individual's need for appropriate pain relief in terms of pulse frequency, pulse width, and pulse amplitude. Thus, a signal provided by system 100 can be tailored for the individual. Controller 32 can include a digital signal processor, a microprocessor, a microcontroller, logic circuitry, and analog circuitry to generate the appropriate signal. The post-operative pain inhibitor (PPI) comprising controller 32 and leads 25 and 27 integrates electrically mediated pain relief and can be controlled by the patient and modify the pulse amplitude, width, wave shape, repetition rate, and zone migration frequency as it relates to their pain threshold. In at least one embodiment leads 25 or 27, or other sensing structures in contact with the patient's body, can be a device to monitor perspiration, heat, modify impulses to affect swelling, EMG integration, and monitor inflammatory markers.

Figure 2:
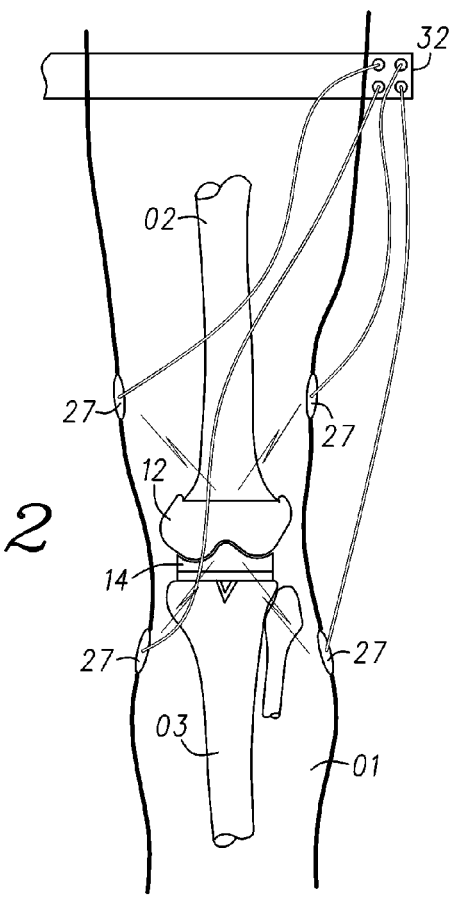
FIG. 2 is an anteroposterior view of a leg in accordance with an exemplary embodiment.

FIG. 2 is an anteroposterior view of a leg in accordance with an exemplary embodiment. The anteroposterior view illustrates positioning of the post-operative pain inhibitor system 100 in relation to the leg, operative field, and joint implant 10. Controller 32 is attached by a belt to the patient. Controls of controller 32 are easily accessible to the patient to modify the signals output by neuro-stimulator circuitry residing therein. Topical leads 27 and percutaneous leads 25 are electrically coupled to skin 1 to provide a signal to peripheral nerve fibers. Topical lead leads 27 are attached and positioned in proximity to femoral implant 12 on both the medial and lateral sides of the knee. Percutaneous leads 25 includes a point that punctures the skin (for better contact) and are positioned in proximity to tibial implant 14 on both the medial and lateral sides of the knee. Topical leads 27 and percutaneous leads 25 are within the operative field of the implanted joint. Both types of leads 25 and 27 can be used to transfer pulses of electrical energy and stimulate peripheral nerve fibers to inhibit propagation of body generated action potentials related to pain. As shown, leads 25 and 27 are connected to controller 32 by a wire. Controller 32 outputs electrical pulses that travel through the external wires to an attachment point on each of leads 25 and 27. Controller 32 is portable and can be powered by a wired power supply, battery, rechargeable battery, or other powering scheme. The portability allows the patient to actively use post-operative pain inhibitor system 100 during a rehabilitation process.

Figure 3:
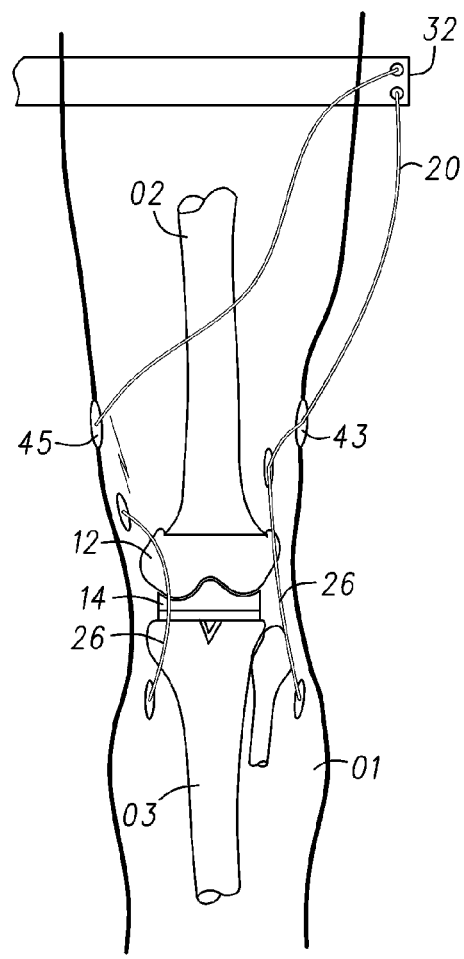
FIG. 3 illustrates an anteroposterior view of a post-operative pain inhibitor system 100 for post-operative pain treatment of the skeletal system in accordance with an exemplary embodiment.

FIG. 3 illustrates an anteroposterior view of a post-operative pain inhibitor system 100 for post-operative pain treatment of the skeletal system in accordance with an exemplary embodiment. The anteroposterior view illustrates positioning of the post-operative pain inhibitor system 100 in relation to the leg, operative field, and joint implant 10. Controller 32 is attached by a belt to the waist of the patient. Controls of controller 32 are easily accessible to the patient to modify the signals output by neuro-stimulator circuitry residing therein. Subcutaneous leads 26 underlie skin 1 and can be positioned close to peripheral nerve fibers to enhance the efficacy of pain modulation. Subcutaneous leads 26 can be placed in the tissue during the implantation of femoral implant 12 and tibial implant 14 respectively to femur 2 and tibia 3. The surgeon can view the operative field and map the region for optimal placement of subcutaneous leads 26 resulting in lower power utilization and better pain control. In a non-limiting example, leads 26 are shown positioned in proximity to femoral implant 12 on both the medial and lateral sides of the knee and in proximity to tibial implant 14 on both the medial and lateral sides of the knee.

In at least one exemplary embodiment, a transmitter/receiver 43 is used to communicate to controller 32 and subcutaneous leads 26. Transmitter/receiver 43 is in a housing affixed to skin 1 in proximity to leads 26. Transmitter/receiver 43 can include neuro-stimulator circuitry to generate a signal for blocking propagation of body generated action potentials. In at least one exemplary embodiment, controller 32 is in wireless communication with transmitter/receiver 43. Controller 32 includes an interface to allow the patient to adjust the pulse amplitude, width, wave shape, repetition rate, and zone migration frequency in conjunction with transmitter/receiver 43. Alternatively, transmitter/receiver 43 can be wired to controller 32. Transmitter/receiver 43 radiates pulses of electrical energy to an implanted conductor with one or more subcutaneous leads 26 positioned in the vicinity of femoral implant 12 and tibial implant 14 to provide effective peripheral nerve stimulation. In an alternate embodiment, a hub 45 can be affixed to the patient's skin 1. Hub 45 is directly connected to an implanted conductor with one or more subcutaneous leads 26 positioned in the vicinity of femoral implant 12 and tibial implant 14 to provide effective peripheral nerve stimulation.

Figure 4:
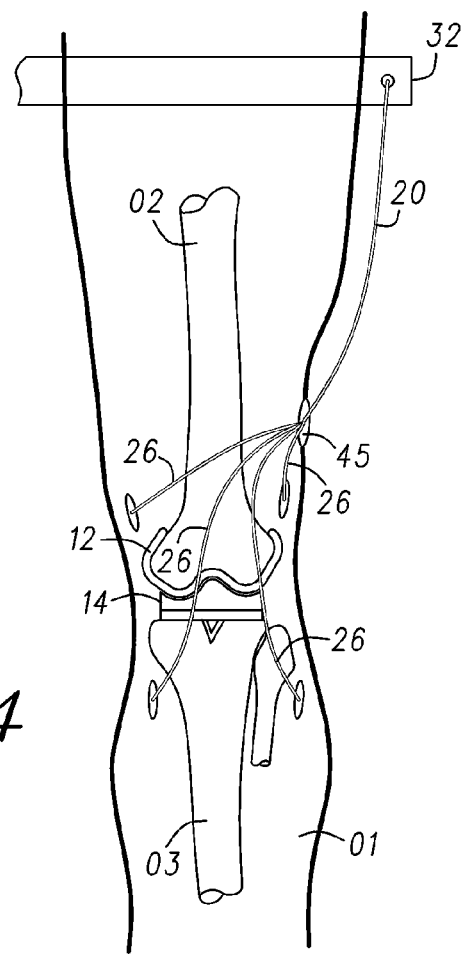
FIG. 4 is a lateral view of a post-operative pain inhibitor system in accordance with an exemplary embodiment.

FIG. 4 is a lateral view of post-operative pain inhibitor system 100 in accordance with an exemplary embodiment. The lateral view illustrates positioning of the post-operative pain inhibitor system 100 in relation to the leg, operative field, and joint implant 10. Controller 32 is attached by a belt to the waist of the patient. Controls of controller 32 are easily accessible to the patient to modify the signals output by neuro-stimulator circuitry residing therein. Subcutaneous leads 26 underlie skin 1 and can be positioned close to peripheral nerve fibers to enhance the efficacy of pain modulation. In a non-limiting example, leads 26 are shown positioned in proximity to femoral implant 12 on both the medial and lateral sides of the knee and in proximity to tibial implant 14 on both the medial and lateral sides of the knee. In a non-limiting example, leads 26 are shown positioned in proximity to femoral implant 12 on both the medial and lateral sides of the knee and in proximity to tibial implant 14 on both the medial and lateral sides of the knee.

Figure 5:
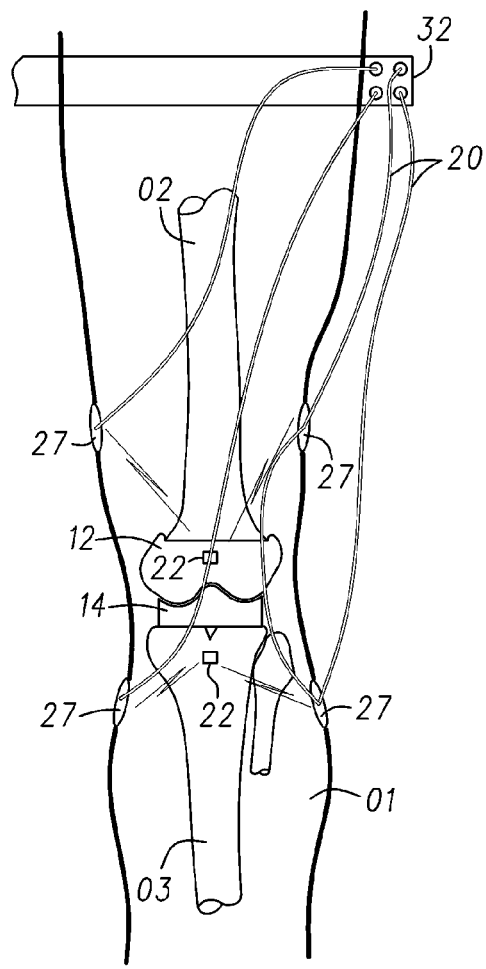
FIG. 5 illustrates an anteroposterior view of a post-operative pain inhibitor system 100 for post-operative pain treatment of the skeletal system in accordance with an exemplary embodiment.

FIG. 5 illustrates an anteroposterior view of a post-operative pain inhibitor system 100 for post-operative pain treatment of the skeletal system in accordance with an exemplary embodiment. Controller 32 is attached by a belt to the waist of the patient. Controls of controller 32 are easily accessible to the patient to modify the signals output by neuro-stimulator circuitry residing therein. In at least one exemplary embodiment, system 100 includes an addition of intraosseous leads 22 to enhance the efficacy of pain modulation. Intraosseous leads 22 are respectively coupled to femur 2 and tibia 3. In a non-limiting example, intraosseous leads 22 can be attached to or inserted in bone during the implantation of an orthopedic joint. In general, intraosseous leads 22 are attached to bone of the skeletal system in proximity to a peripheral nerve fiber.

In at least one exemplary embodiment, topical leads 27 can include transmitters to radiate pulses of electrical energy to implanted intraosseous leads 22. Topical leads are connected by wire to controller 32. Topical leads 27 are placed in proximity to intraosseous leads 22. More specifically, one or more topical leads 27 having transmitters are positioned on skin 1 of the patient in proximity to the distal end of the femur 2 where a first intraosseous lead 22 resides. Similarly, two additional topical leads 27 having transmitters are positioned on the skin 1 of the patient in proximity proximal end of tibia 3 where a second intraosseous lead 22 resides. Each topical lead 27 radiates pulses of electrical energy to an implanted conductor within intraosseous leads 22. The pulsed electrical energy is received by intraosseous leads 22 and conducted within the bone to create an operative field stimulating the peripheral nerve fiber to block propagation of body generated action potentials corresponding to pain. The patient can change or modify the signal provided to intraosseous leads 22 by modifying pulse amplitude, pulse width, wave shape, repetition rate, and zone migration frequency using controller 32 thereby affecting perceived pain to the patient and tailoring the signal for the individual.

Alternatively, intraosseous leads 22 can include a transmitter/receiver and a power source such as a battery. An external powering coil could also be used to energize intraosseous leads 22 or to recharge the battery. Intraosseous leads 22 can be in wireless communication with topical leads 27 or controller 32. Using low amplitude current pulses to block the body generated action potentials system 100 could be operated over a significant period of time.

Figure 6:
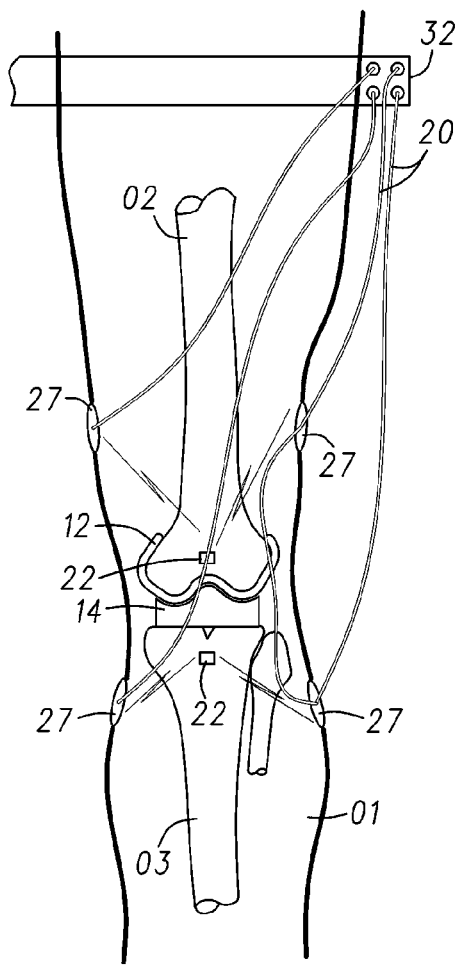
FIG. 6 is a lateral view of post-operative pain inhibitor system in accordance with an exemplary embodiment.

FIG. 6 is a lateral view of post-operative pain inhibitor system 100 in accordance with an exemplary embodiment. The lateral view illustrates positioning of the post-operative pain inhibitor system 100 in relation to the leg, operative field, and joint implant 10. Controller 32 is attached by a belt to the waist of the patient. Controls of controller 32 are easily accessible to the patient to modify the signals output by neuro-stimulator circuitry residing therein. Intraosseous leads 22 are attached to femur 2 and tibia 3 close to peripheral nerve fibers to enhance the efficacy of pain modulation. In a non-limiting example, leads 27 are shown positioned in proximity to the distal end of femur 2 and proximal end of tibia 3 on both the medial and lateral sides of the knee. Controller 32 is in wired communication with topical leads 27 while topical leads are in wireless communication with intraosseous leads 22 as described hereinabove.

Figure 7:
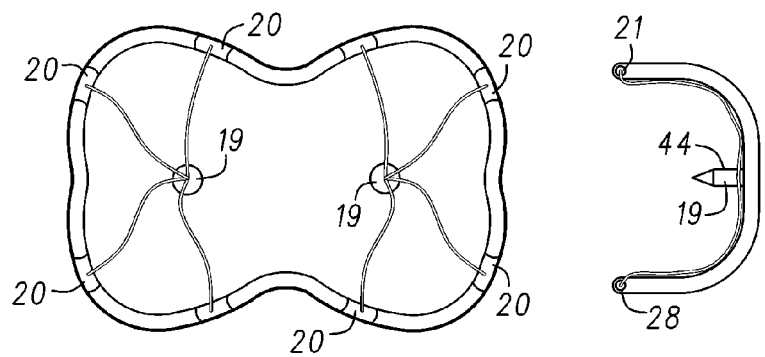
FIG. 7 is an illustration of a prosthetic component having integrated electrical leads to provide a signal to a peripheral nerve fiber to reduce post-operative pain.

FIG. 7 is an illustration of a prosthetic component having integrated electrical leads to provide a signal to a peripheral nerve fiber to reduce post-operative pain. In a non-limiting example, the prosthetic component is femoral implant 12. In general, a distal end of femur 2 is prepared and shaped to receive femoral implant 12. In at least one exemplary embodiment, a profile of femoral implant 12 is shaped similar to existing implants being offered such that the device can be installed using procedures and practices known to the surgeon. Although shown as femoral implant 12, the principles and structures described herein can be applied to a wide range of orthopedic prosthesis as well as other implanted medical devices.

An antereoposterior view of femoral implant 12 is shown. The illustration is viewed towards the condyle surfaces of femoral implant 12. Circuitry 44, within or underlying peg lugs 19 is coupled with leads 20 through an electrical interconnect. In an non-limiting example, the interconnect can be wire, flex interconnect, or other suitable electrically conducting material. The interconnect connects from peg lugs 19 to leads 20. Leads 20 are exposed on the surface of the prosthetic component. Leads 20 are positioned around a peripheral surface at a distal end of femoral implant 12. The location is such that leads 20 are exposed through most or all of a lower leg rotation. In at least one exemplary embodiment, peg lugs 19 extend into an interior surface of femoral implant 12. The lateral view of femoral implant 12 illustrates peg lugs 19 extending from the surface of femoral implant 12. Femoral implant 12 is C-shaped having an outer surface that mimics a natural condyle surface. The interconnect is placed overlying or interior to the internal surface of femoral implant 12 connecting peg lugs 19 to leads 20.

Many neuro-stimulation procedures require precise positioning of electrical leads. Similarly, an orthopedic joint implant requires precise positioning of the prosthesis components to the skeletal system corresponding to location, distance, relational bone to bone positioning, balance, and alignment. Integration of leads 20 into a prosthesis component takes advantage of this precise positioning within the body that is a very repeatable and consistent procedure. Thus, integration of leads 20 on the surface of a prosthetic component, or components, or within a prosthetic components, enables accurate placement of the leads automatically with the same high level of accuracy as the placement of the prosthesis itself. There is no added surgical time to incorporate the post-operative pain inhibitor since it is incorporated in the implant thereby minimizing stress on the patient. Moreover, this reduces cost because the device can be implemented without requiring the assistance of a neurosurgeon. Ultimately, the patient benefits of less post operative pain (under user control) and faster recovery are achieved with minimal impact to the complexity, cost, and length of the surgery.

Circuitry 44 can further comprise additional circuitry that is placed in femoral implant 12. Circuitry 44 can process a received signal from controller 32 to support driving leads 20 to output a pulsed signal appropriate to stimulate a peripheral nerve fiber in proximity to leads 20 to block a body generated pain signal. The pulsed signal output by leads 20 can be processed or modified in different ways. In a first embodiment, processing by circuitry 44 is minimal with leads 20 directly connected to neuro-stimulator circuitry external to the patient through a transcutaneous lead. The neuro-stimulator circuitry can be located in controller 32 or on or near the transcutaneous lead. In a second embodiment, one or more topical leads having a transmitter that is connected to neuro-stimulator circuitry external to the patient. The topical leads are affixed to the skin 1 of the patient in proximity to femoral implant 12. Pulses of electrical energy corresponding to a signal provided to the peripheral nerve fiber are coupled wirelessly to circuitry 44 integrated into the femoral component 12. In a third embodiment, circuitry 44 can further comprise a power source and neuro-stimulator circuitry to control pain under control of the patient controller 32. The neuro-stimulator circuitry is located in femoral implant 12 and can generate appropriate waveforms under patient control to stimulate the peripheral nerve fibers to reduce pain.

In at least one exemplary embodiment, circuitry 44 is integrated within the femoral component 12 and positioned within or underlying peg lugs 19. A receiver circuit of circuitry 44 can be embedded within the femoral component 12 to wirelessly couple electrical energy radiated by an external source, such as, but not limited to, an induction loop or antenna. The energy received by the induction loop or antenna can be coupled directly to transmitter circuitry of circuitry 44 that is provided to leads 20 to be radiated to the peripheral nerve fiber. Circuitry 44 can further comprise energy storage capacity that includes, but is not limited to, a battery, capacitor, super capacitor, supercapacitor, ultra cap, ultra capacitor, ultracapacitor, or means of continuous reception of external energy. The embedded receiver can be coupled to the energy storage capacity to power circuitry 44 and more specifically neuro-stimulation circuitry in femoral implant 12. The output of the neuro-stimulation circuitry is coupled to the leads 20 to provide the pain blocking waveform to the peripheral nerve fiber.

Another variation is the integration of an intraosseous lead or leads into the tip or tips of the peg lugs 19. The intraosseous leads can be included in addition to the leads on the perimeter of femoral implant 12 to supplement coupling of the stimulation signal to the peripheral nerve fiber. Intraosseous leads can also be used in place of the leads 20 to output a signal that stimulates the peripheral nerve fiber. The intraosseous leads are under the control of controller 32 as are leads 20.

Figure 8:
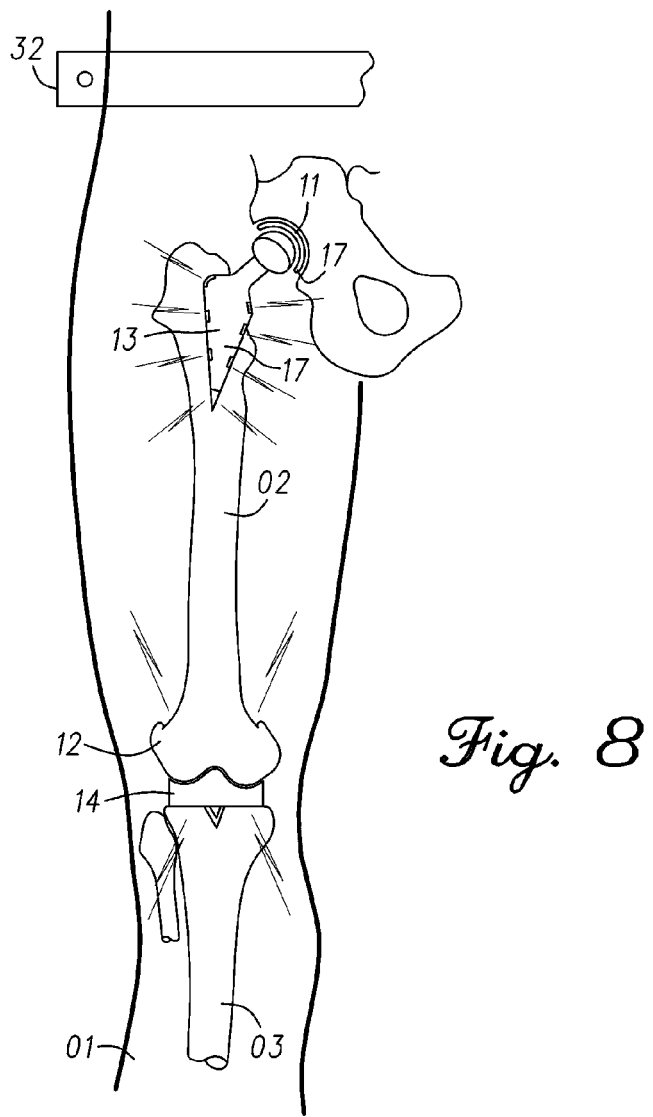
FIG. 8 is an illustration of components of a post-operative pain inhibitor system integrated into more than one prosthetic components.

FIG. 8 is an illustration of components of a post-operative pain inhibitor system 100 integrated into more than one prosthetic components. As mentioned previously, incorporating leads into an orthopedic implant component to stimulate peripheral nerve fibers for reducing pain is beneficial because of proximity to the operative field and peripheral nerve fibers as well as the precise positioning of the component. There may be situations where patients require multiple joint prostheses to raise their quality of life. In such instances, post-operative pain inhibitor system can be used in conjunction with each implanted component. In at least one exemplary embodiment, a single patient controller 32 can control each implanted component having integrated leads to affect body generated potentials in proximity to each implanted region.

A leg is illustrated having both a hip implant and a knee implant. The knee implant has been described in detail hereinabove. A hip replacement typically comprises a cup 11, a bearing, and a femoral implant 13. In at least one exemplary embodiment, cup 11 comprises metal or other material of high strength. The surgeon reams out the acetabulum area of the pelvis to fit cup 11. The fitting of cup 11 requires precise positioning in the reamed out acetabulum and is typically a compression fitting. The bearing is then fitted into cup 11 for providing a low friction low wear surface in which a femoral head of femoral implant 13 is fitted. The bearing typically comprises a polymer material such as ultra high molecular weight polyethylene. In general, a predetermined amount of surface area of femoral head is in contact with the surface of bearing to minimize loading and wear on the material. The surgeon prepares femur 2 to receive and retain femoral implant 13. Femoral implant 13 is fastened into a proximal end of femur 2. Femoral implant 13 comprises a strong lightweight material and typically comprises a metal or metal alloy. The hip and knee replacement components are selected to be formed of biologically compatible materials.

Femoral implant 12 and tibial implant 14 of the knee implant include circuitry and leads to stimulate peripheral nerve fibers in proximity to the operative field of the knee. Similarly, femoral implant 13 includes circuitry and leads to stimulate peripheral nerve fibers in proximity to the operative field of the hip. As disclosed above, controller 32 is operatively coupled to provide a signal to the leads of femoral implant 13, femoral implant 12, and tibial implant 14. Controller 32 further provides patient control of the signal provided to each implant thereby allowing the patient to tailor the signal waveform to minimize perceived pain in the knee and hip regions. The anteroposterior view illustrates the relative positions of cup 11, femoral implant 13, femoral implant 12, and tibial implant 14. The example illustrates post-operative pain inhibitor system 100 having more than one active component but is not limited to multiple device applications.

Figure 9:
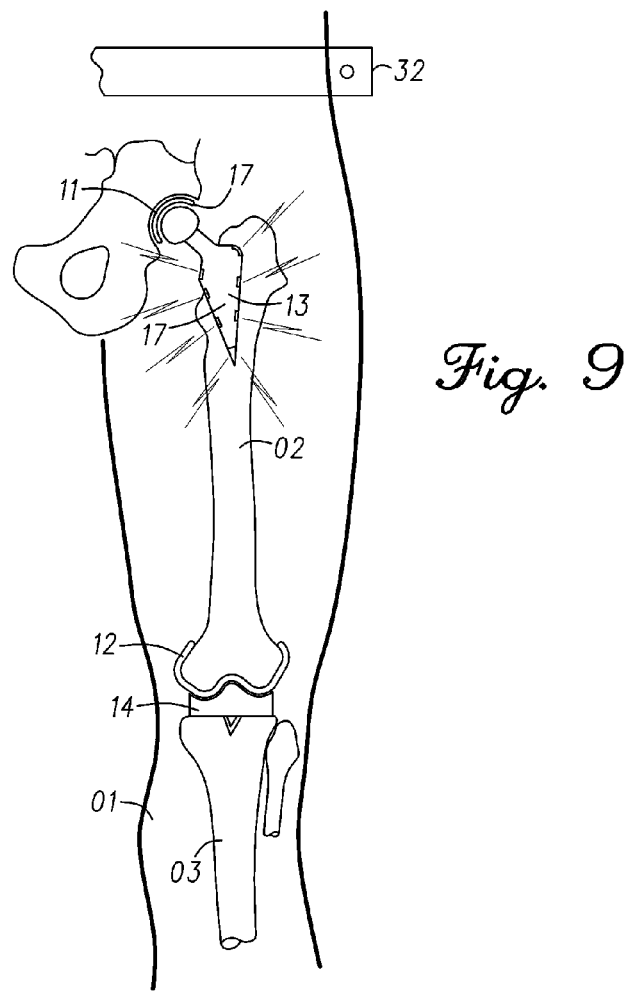
FIG. 9 is a lateral view of post-operative pain inhibitor system in accordance with an exemplary embodiment, additionally

FIG. 9 is a lateral view of post-operative pain inhibitor system 100 in accordance with an exemplary embodiment. The lateral view illustrates positioning of the post-operative pain inhibitor system 100 in relation to the leg, operative field, and joint implant 10. Controller 32 is attached by a belt to the waist of the patient. Controls of controller 32 are easily accessible to the patient to modify the signals output by neuro-stimulator circuitry residing therein. The lateral view illustrates femoral implant 13 in a hip region. It also illustrates femoral implant 14 and tibial implant 12 in the knee region. The implants have leads that are exposed in periodic spacing circumferentially around the implant to maximize signal coverage. Alternatively, the leads can be placed in specific locations that are in proximity to a peripheral nerve.

Figure 10:
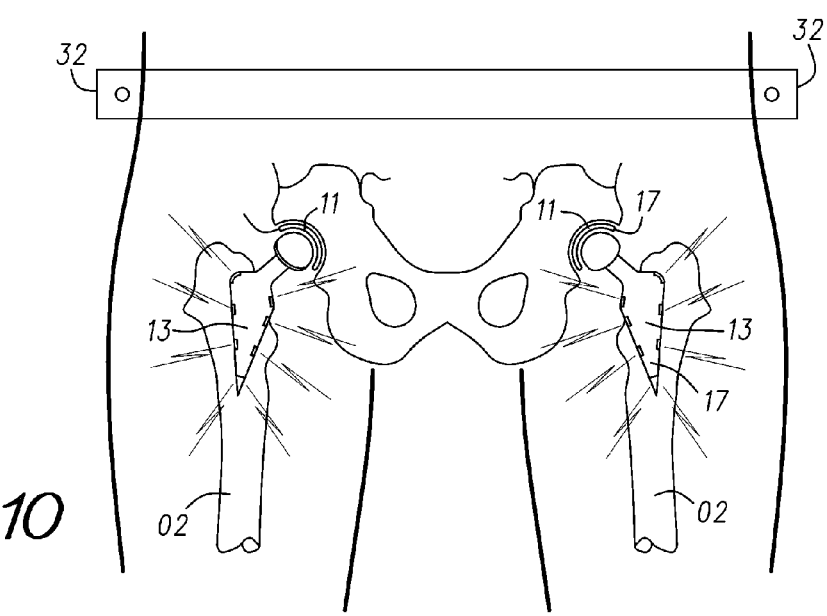
FIGS. 10 and 11 illustrate additional exemplary embodiments.

FIG. 10 is an illustration of hip prosthesis 17 in accordance with an exemplary embodiment. Each leg has femoral implant 13 coupled to a proximal end of femur 2. Each femoral implant 13 includes leads for coupling to a peripheral nerve fiber in proximity to the joint implant. As disclosed hereinabove, femoral implant 13 can house circuitry and a power supply. Controller 32 is coupled to the leads of each femoral implant for providing a signal. The signal can be controlled by the patient. The leads of each implant output the signal to block body generated action potential in the peripheral nerve corresponding to a pain signal. Controller 32 can modify the signal under user control to each femoral implant 13 to a waveform that minimizes perceived pain for each leg in proximity to the hip region.

In general, an invasive procedure such as hip surgery causes chemicals in the body to be released due to the incision and subsequent damage to the surrounding tissue as the bone is modified and the implants put in place. The bodily generated chemicals greatly sensitize the local nociceptors causing substantial pain to the patient. Gate theory implies that the bodily generated action potentials propagating to the peripheral nerve fibers can be opened or closed. Post-operative pain inhibitor system 100 reduces the propagation of the signals by stimulating the peripheral nerve fibers to close the gate. As mentioned previously, the signal coupled to the peripheral nerve fibers are low current pulses. In general, a typical frequency of the pulses are in the range of 100-200 Hz.

The circuitry placed in femoral implant 13 comprises a power source, such as a battery and electronic circuitry to energize electrical leads or to radiate electrical stimuli into the field of stimulation. The latter circuitry is referred to as a transmitter. Wireless nerve stimulators can be powered by receiving externally generated electrical energy as input to the transmitter. This receiving circuitry is referred to as a receiver. The provided energy can be continuous or intermittent. If the energy is provided intermittently, a capacity for storing electrical energy can be used such as a battery, capacitor, or inductor.

Figure 11:
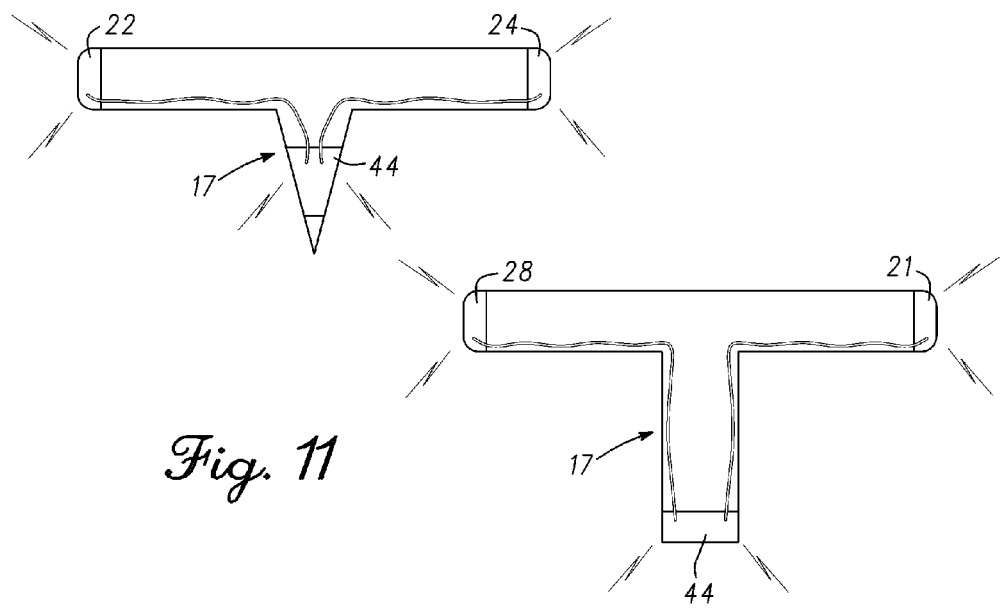

FIG. 11 is an illustration of a tibial implant 14 in accordance with an exemplary embodiment. Tibial implant 14 is a support and retaining structure for the insert. Leads 21, 22, 24, and 28 are integrated into tibial implant 14. The anteroposterior and lateral views of the tibial component illustrates the placement of the leads 21, 23, 24, and 28 that are exposed on the perimeter of the tibial component 14. The leads couple to neuro-stimulation circuitry in one of tibial implant 14, a housing attached to skin 1, or in controller 32. Leads 21, 23, 24, and 28 provide signals to peripheral nerve fibers to block body generated action potentials under patient control via controller 32. Circuitry 44 can be integrated in many locations within the tibial implant 14. In one embodiment, circuitry 44 is housed in stem 17 of tibial implant 14.

In at least one exemplary embodiment, an intraosseous lead or leads are positioned on or integrated within the tip (not shown) of the stem 17 of the tibial implant 14. In one embodiment, the intraosseous leads are in addition to leads 21, 23, 24, 28 on the perimeter of the tibial component 14. In a second embodiment the intraosseous leads can be used in place of one or more leads 21, 23, 24, and 28. The intraosseous leads provide a conductive field of operation that provides effective peripheral nerve stimulation.

Figure 12:
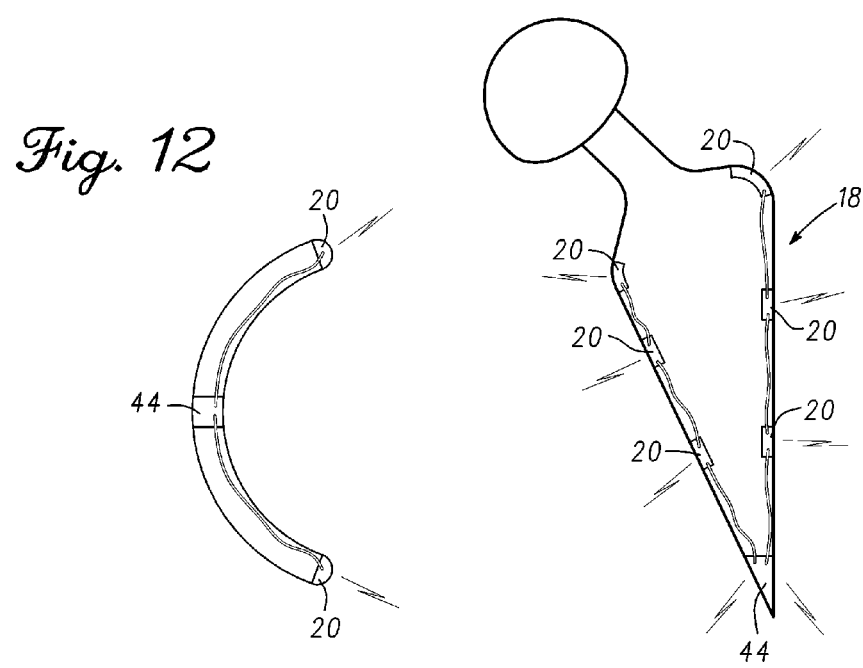
FIG. 12 is an illustration of a femoral implant and cup implant in accordance with an exemplary embodiment.

FIG. 12 is an illustration of a femoral implant 13 and cup implant 11 in accordance with an exemplary embodiment.

Cup implant 11 is also known as an acetabulum component. The anteroposterior view of femoral implant 13 illustrates exposed leads positioned circumferentially and in different areas of implant 13. The leads are connected by wire to circuitry 44 that can be formed in, internal to, or external to femoral implant 13. As shown, wires are placed along the sides of the stem 18 of the femoral implant 13 or integrated within the perimeter of the stem 18 of the femoral implant 13 of the hip prosthesis. In a non-limiting example, circuitry 44 can be placed in a tip region of femoral implant 13. Circuitry 44 can include a power source and a transmitter/receiver. Circuitry 44 in conjunction with the exposed leads generates a field of operation that provides effective peripheral nerve stimulation. The nerve stimulation can be modified using patient controller 32.

The lateral view of cup 11 illustrates the placement of leads 20 positioned on or integrated into the perimeter of the cup 11. Circuitry 44 can be integrated in many locations within the cup 11. In a non-limiting example, circuitry 44 is shown in a central region of cup 11.

A further variation includes intraosseous lead or leads positioned on or integrated within the tip of stem 18 of the femoral component 13. In a first embodiment the intraosseous lead or leads are addition to the leads on the perimeter of femoral implant 13. In a second embodiment, intraosseous leads are used solely to create an operative field that provides effective peripheral nerve fiber stimulation in conjunction with external patient controller 32.

Figure 13:
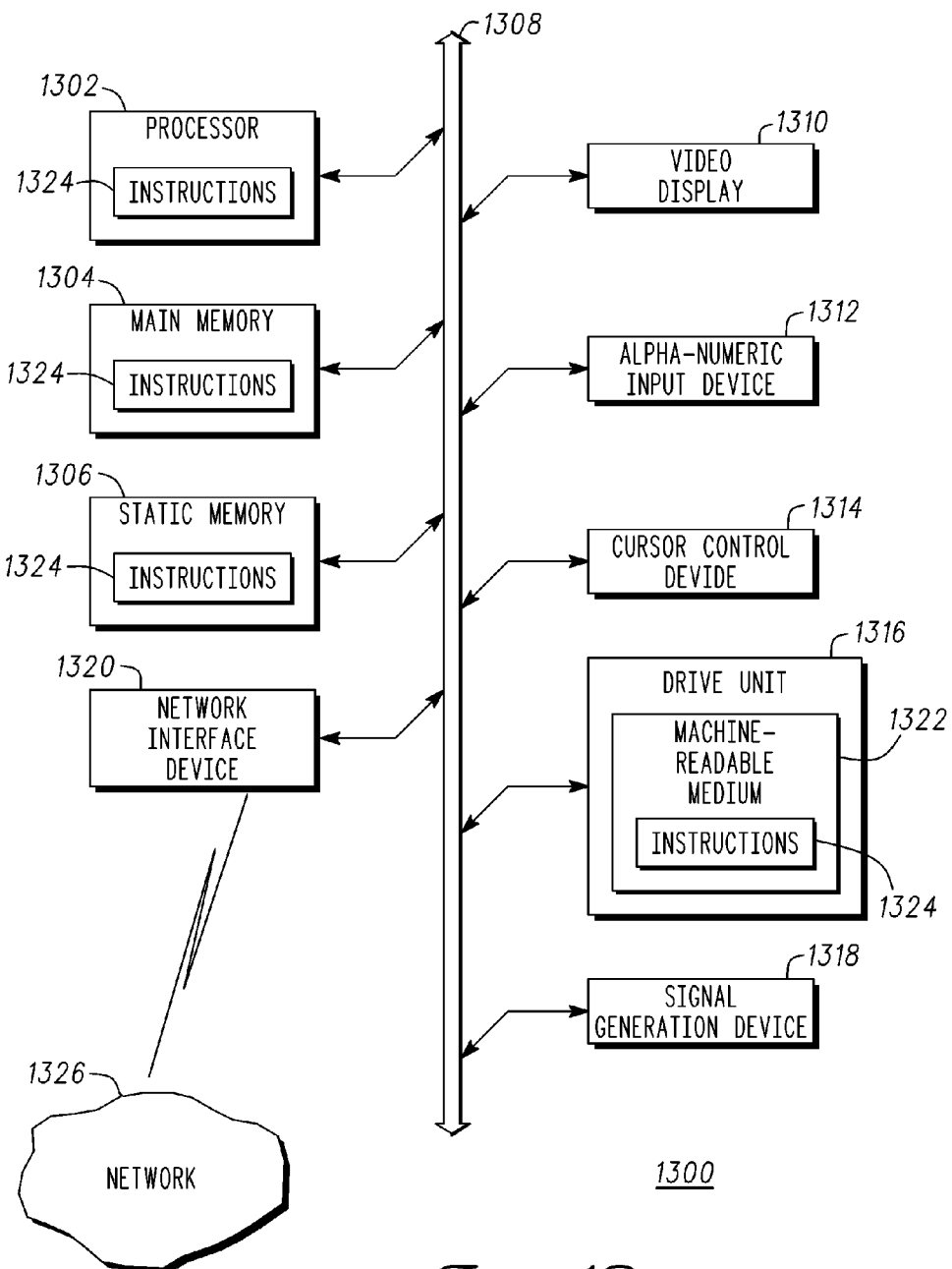
FIG. 13 depicts an exemplary diagrammatic representation of a machine in the form of a computer system within which a set of instructions, when executed, may cause the machine to perform any one or more of the methodologies discussed above.

FIG. 13 depicts an exemplary diagrammatic representation of a machine in the form of a computer system 1300 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 1300 may include a processor 1302 (e.g., a central processing unit (CPU), a graphics processing unit (GPU, or both), a main memory 1304 and a static memory 1306, which communicate with each other via a bus 1308. The computer system 1300 may further include a video display unit 1310 (e.g., a liquid crystal display (LCD), a flat panel, a solid state display, or a cathode ray tube (CRT)). The computer system 1300 may include an input device 1312 (e.g., a keyboard), a cursor control device 1314 (e.g., a mouse), a disk drive unit 1316, a signal generation device 1318 (e.g., a speaker or remote control) and a network interface device 1320.

The disk drive unit 1316 can be other types of memory such as flash memory and may include a machine-readable medium 1322 on which is stored one or more sets of instructions (e.g., software 1324) embodying any one or more of the methodologies or functions described herein, including those methods illustrated above. The instructions 1324 may also reside, completely or at least partially, within the main memory 1304, the static memory 1306, and/or within the processor 1302 during execution thereof by the computer system 1300. The main memory 1304 and the processor 1302 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 1324, or that which receives and executes instructions 1324 from a propagated signal so that a device connected to a network environment 1326 can send or receive voice, video or data, and to communicate over the network 1326 using the instructions 1324. The instructions 1324 may further be transmitted or received over a network 1326 via the network interface device 1320.

While the machine-readable medium 1322 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

By now it should be appreciated that various embodiments of a post-operative pain inhibitor system has been described. In particular, the PPI provides substantial benefit in reducing post-surgical pain after a joint replacement. Reducing pain alleviates patient stress and can accelerate the rehabilitation process. Post-operative pain inhibitors may be applied to a wide range of surgeries and implanted medical devices. These include shoulder, elbow, wrist, hand, spine, and ankle surgeries and prosthetic devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A post-operative pain inhibitor system configured for post-operative treatment of a surgically implanted joint comprising:
    an electrode configured to attach to skin in proximity to the implanted joint; and
    a controller operatively configured to couple to the electrode, where the controller is configured to provide energy pulses to the electrode and where the controller is configured to control the energy pulses where the system is configured to stimulate nerve bundles in proximity to an operative field of the implanted joint.

2. The system of claim 1 further including at least one prosthetic component of the implanted joint having at least one electrode configured to provide energy pulses.

3. The system of claim 2, where the controller is configured to modify at least one of pulse width, pulse shape, pulse repetition rate, and pulse amplitude.

4. The system of claim 1 further including one or more sensors configured to couple to the controller to monitor at least one of temperature, perspiration, inflammatory markers, electromyogram signals, and swelling.

5. The system of claim 1 further including at least one electrode configured to subcutaneously couple in proximity to the operative field.

6. The system of claim 1 further including at least one electrode configured to percutaneously couple in proximity to the operative field.

7. The system of claim 1 further including at least one electrode configured to intraosseously couple in proximity to the operative field.

8. A post-operative pain inhibitor system configured for post-operative treatment of an implanted joint comprising:
    a transmitter;
    a power source coupled to the transmitter;
    an electrode configured to couple to the transmitter where the electrode is in proximity to the implanted joint; and
    a prosthetic component where one of the transmitter or power source is housed in the prosthetic component.

9. The system of claim 8 further including a receiver coupled to the power source.

10. The system of claim 9 where the receiver is configured to receive energy wirelessly.

11. The system of claim 10 where the prosthetic component further comprises the at least one electrode.

12. The system of claim 8 further including a controller configured to be coupled to at least one electrode where the controller is configured to modify at least one of the pulse width, pulse repetition rate, pulse shape, or pulse amplitude.

13. The system of claim 8 further including further including at least one electrode configured to subcutaneously couple in proximity to the operative field.

14. The system of claim 8 further including at least one electrode configured to percutaneously couple in proximity to the operative field.

15. The system of claim 8 further including at least one electrode configured to intraosseously couple in proximity to the operative field.

16. A post-operative pain inhibitor system configured for post-operative treatment of a knee joint implant comprising:
    a controller;
    a prosthetic knee component;
    an electrode where the electrode is configured to attach to skin in proximity to the component, where the controller is configured to couple to the electrode, and where the controller is configured to modify at least one of pulse width, pulse shape, pulse repetition rate, and pulse amplitude;
    a transmitter coupled to an electrode; and
    a power source coupled to the transmitter where one of the transmitter or power source is housed in the prosthetic knee component.

17. The system of claim 16 further including at least one electrode on the prosthetic knee component configured to deliver energy pulses where the controller is configured to couple to the at least one electrode on the prosthetic component.

18. The system of claim 16 further including a receiver coupled to the power source where the receiver is configured to receive energy wirelessly.

* * * * *